United States Patent [19]
Chain et al.

[11] 3,966,707
[45] June 29, 1976

[54] PROCESS FOR PREPARING DOUBLE STRANDED RNA

[75] Inventors: Ernst Boris Chain, London; Kenneth William Buck, Crawley Down; Joan Elizabeth Darbyshire, London; Geoffrey Talbot Banks, Billingshurst; Fred Himmelweit; Giulio Ratti, both of London, all of England

[73] Assignee: Beecham Group Limited, United Kingdom

[22] Filed: Aug. 2, 1974

[21] Appl. No.: 494,334

Related U.S. Application Data

[60] Continuation of Ser. No. 202,635, Nov. 26, 1971, abandoned, which is a division of Ser. No. 124,496, March 15, 1971, abandoned.

[52] U.S. Cl............................ 260/211.5 R; 195/15; 195/28 N; 424/85
[51] Int. Cl.².......................................... C07C 21/02
[58] Field of Search............................. 260/211.5 R

[56] References Cited
UNITED STATES PATENTS

| | | | |
|---|---|---|---|
| 3,597,318 | 8/1971 | Sutherland et al. | 260/211.5 R |
| 3,629,235 | 12/1971 | Lampson et al. | 260/211.5 R |

OTHER PUBLICATIONS

Moyer et al., "Chem. Abst.", vol. 60, p. 10968(b), 1964.

*Primary Examiner*—Johnnie R. Brown

[57] ABSTRACT

Virus particles capable of stimulating the production of interferon are isolated from fungal cells of the mould *Aspergillus foetidus* or *Aspergillus niger* or from the nutrient medium in which or on which *Aspergillus foetidus* or *Aspergillus niger* mould has been grown. Double-stranded RNA material can be isolated from the virus particles extracted from *Aspergillus foetidus* or *Aspergillus niger* and said RNA material is capable of stimulating production of interferon. Pharmaceutical compositions comprising said particles or said RNA material in combination with pharmaceutically acceptable carriers and excipients are also provided.

6 Claims, No Drawings

PROCESS FOR PREPARING DOUBLE STRANDED RNA

This is a continuation of application Ser. No. 202,635 filed Nov. 26, 1971, which is a division of Ser. No. 124,496 filed Mar. 15, 1971 both now abandoned.

This invention relates to antiviral materials and to a process for the isolation of such materials. More particularly it concerns a therapeutic and/or prophylactic composition comprising an antiviral material which is extracted from the fungal cells of the mould *Aspergillus foetidus* or *Aspergillus niger* or from a nutrient medium in which or on which *Aspergillus foetidus* or *Aspergillus niger* has been cultivated.

It is known that an antiviral nucleic acid material can be isolated from certain penicillin producing strains of *Penicillium chrysogenum* (British patent specification No. 1,170,929). Virus particles with interferon stimulating properties have been found in a strain of *Penicillium stoloniferum* and a strain of *Penicillium funiculosum*. More recently virus particles have been isolated from a strain of *Penicillium cyaneofulvum*. In certain of the instances cited above it has been shown that the RNA present in the virus particles is the active agent in stimulating the production of interferon. It has also been shown that the RNA isolated from the viruses which is active in stimulating interferon is double-stranded.

The present invention provides in one of its embodiments, virus particles capable of stimulating the production of interferon in animals said virus particles being isolatable from the fungal cells of the mould *Aspergillus foetidus* or *Aspergillus niger* or from the nutrient medium in which or on which the mould *Aspergillus foetidus* or *Aspergillus niger* has been grown.

The strain of *Aspergillus foetidus* employed as a source of virus particles may be one designated IMI 41871 (Commonwealth Mycological Institute, Kew, Surrey, England).

The strain of *Aspergillus niger* employed as a source of virus particles may be one designated IMI 146891. In the present specification the term "virus particles" refers to the polyhedral particles which are found in a nutrient medium on which or in which the mould *Aspergillus foetidus* or *Aspergillus niger* has been grown, or which are found in the cells of the mould *Aspergillus foetidus* or *Aspergillus niger* itself. These particles satisfy all the criteria, except demonstratable infectivity, normally characteristic of a virus, e.g. characteristic morphology and staining in electron micrographs, sedimentation patterns typical of small isometric viruses during density gradient and analytical centrifugation, specific serological reactions and ultra violet absorption spectra typical of viral nucleoproteins. The virus particles referred to can be obtained either from the mycelium of the mould itself or by suitable extraction of the culture medium in which or on which the mould has been grown.

Tests have shown that the virus particles extracted from *Aspergillus foetidus* and *Aspergillus niger* are not serologically related to the viruses known from *Penicillium stoloniferum*, *Penicillium funiculosum*, *Penicillium cyaneofulvum* or *Penicillium chrysogenum*.

In another embodiment of the present invention there is provided a double-stranded ribonucleic acid material isolated from the virus particles extracted from *Aspergillus foetidus* or *Aspergillus niger*, said double-stranded ribonucleic acid material being capable of stimulating production of interferon in animals.

The double-stranded ribonucleic acid material may be a single species or may be a mixture of individual species of double-stranded ribonucleic acid. When *Aspergillus foetidus* IMI 41871 is employed as a source of virus particles, the double-stranded RNA is in fact a mixture of at least four RNA species, as evidenced by the formation of at least four bands on polyacrylamide gel electrophoresis.

In another aspect of the present invention there is provided an antiviral composition which composition comprises the virus particles of this invention and/or the double-stranded ribonucleic acid material of this invention and one or more pharmaceutically acceptable carriers or excipients. Particularly preferred compositions are those suitable for parenteral injection or for intranasal administration, e.g. aerosol formulations.

The virus particles of this invention may be isolated by a process which comprises separating the mycelium of the mould *Aspergillus foetidus* or *Aspergillus niger* from a culture medium in which or on which it has been grown, treating the culture medium with ribonucleic acid or a salt thereof, adjusting the pH of the resulting liquor to a pH between 3 and 6, separating the resulting precipitate from the supernatant, and concentrating and purifying a neutralised suspension of the precipitate to yield the desired virus particles. The suspension of the precipitate may be purified by differential sedimentation.

The virus particles of this invention may also be prepared by a process which comprises disrupting the mycelium of the mould *Aspergillus foetidus* or *Aspergillus niger* to release the cell contents, removing the cell debris from a suspension of the disrupted mycelium, treating the remaining liquor with ribonucleic acid or a salt thereof, adjusting the pH of the resulting liquor to a pH between 3 and 6, separating the resulting precipitate from the supernatant, concentrating and purifying a neutralised suspension of the precipitate to yield the desired virus-like particles. Here again the suspension of the precipitate may be purified by differential sedimentation.

In both processes for the isolation of the virus particles of the present invention, ribonucleic acid is employed to form a complex with the virus particles. Any suitable ribonucleic acid may be employed but we prefer to use commercial ribonucleic acid, in the form of its sodium salt, which has been obtained from yeast. After the addition of the ribonucleic acid the virus particles/ribonucleic acid complex is precipitated. This precipitation stage is carried out at a pH from 3 to 6 and preferably about 4.5. The separation of the precipitate from the supernatant can be effected by suitable filtration methods, for example by using a filter press. Generally the precipitated complex can be dissociated by suspending the solids in a suitable medium, and adjusting the pH to between 6.5 and 8.5 preferably about 7.4, whereupon the yeast RNA is dissolved, leaving the virus particles in free form.

Differential sedimentation, rate zonal and isopycnic centrifugal techniques have been well documented and we have found that good results are obtained by ultracentrifugation on a caesium chloride density gradient. The double-stranded RNA material of this invention can be extracted from the virus particles by deproteinisation of the virus particles. The preferred technique for this deproteinisation stage is the treatment of the virus particles with detergent and phenol. For example, sodium dodecyl sulphate can be added to the virus particles and the resulting suspension may be extracted with phenol. Phase separation is then effected by centrifugation and phenol is then removed by extraction with ether. The double-stranded RNA is then precipitated by the addition of a suitable alcoholic medium. The viral RNA obtained in this manner can be shown to have properties associated with double-stranded ribonucleic acids, e.g. characteristic behaviour on heating and treatment with ribonuclease.

Both the virus particles of this invention and the double-stranded RNA obtained from these virus particles have been shown to stimulate the production of interferon in animals.

According to the present invention there is provided a method of protecting animals against virus infections or for the treatment of virus infections in animals, which method comprises administering to the animal virus particles obtained from the fungal cells of the mould *Aspergillus foetidus* or *Aspergillus niger* and/or the double-stranded ribonucleic acid material obtained from said virus particles.

The virus particles and/or double-stranded ribonucleic acid (RNA) may be administered by intraperitoneal injection or any other suitable method. Intranasal administration may be suitable on occasions.

The *Aspergillus foetidus* or *Aspergillus niger* is usually grown on a suitable solid medium for the production of inoculum for a fermentation stage, for example a medium based on a mixture of carbon and nitrogen sources, mineral salts and agar. After inoculation of the agar culture it is allowed to grow at a temperature between about 20°C and 35°C preferably at about 27°C for about one week. A longer growth period is usually undesirable because the culture deteriorates with time, the number of viable cells declining. A suitable medium for the production of inoculants has the following composition:

| | |
|---|---|
| Potato Infusion | 30% |
| Glucose | 3% |
| Agar | 1.5% |
| In distilled water at pH 7.0. | |

The agar medium is dispensed into test tubes or medical flats, closed with cotton wool, sterilised by autoclaving in the usual manner, and allowed to set. For longer term storage, the culture is grown on the above agar medium in screw topped bottles for about a week before covering the entire slope culture with autoclaved liquid paraffin B.C. Under these conditions the culture may be stored at room temperature for several years without loss of viability.

The fermentation stage involves culturing the *Aspergillus foetidus* or *Aspergillus niger* in a suitable nutrient medium under aerobic conditions at a temperature within the range from about 20°C to 35°C preferably 27°C. Suitable nutrient media contain a source of carbon, nitrogen and minerals. A particularly suitable medium is as follows:

| | |
|---|---|
| Glucose | 2.0% |
| Peptone | 0.1% |
| Corn steep liquor | 5.0% |
| Yeast Autolysate | 0.1% |
| Dipotassium hydrogen phosphate | 0.5% |
| Tap water | |

-continued
pH 6.5 sterilised for 40 minutes at 121°.

The fermentation stage is inoculated by using a suspension of fungal cells prepared by scraping the surface of an agar slope culutre described above in the presence of added deionised water. The fermentation medium is usually inoculated with between 1% and 5% of the inoculant suspension of fungal cells.

The fungus is then cultivated in the fermentation stage for from 2 to 8 days at a temperature in the range of about 20°C to 35°C preferably 27°C. Cultures in conical flasks are shaken on a rotary shaker or incubated static; cultures in fermenters are incubated by injecting sterile air through the culture medium. The virus/particles appear to be present in the mould mycelium during the early part of the growth cycle, and we have observed that the highest concentration is present in the mycelium after about 1 to 3 days. After 2 to 4 days the virus particles begin to appear in the culture medium itself and after 4 to 8 days reach a maximum concentration in the medium. Accordingly the virus particles can be extracted from the culture medium after 4 to 8 days from inoculation, or alternatively in about 2 days from the mycelium of the mould itself by disrupting living or killed cells.

Specific embodiments of the present invention will now be described with reference to the following Examples:

EXAMPLE 1

*Aspergillus foetidus* strain IMI 41871 was grown in submerged culture at 27°C for 48 hours in shaken flasks, in a medium containing glucose 2%, peptone (0.1%), corn steep liquor (5%), yeast autolysate (0.1%) and dipotassium hydrogen phosphate (0.5%). The mycelium (10 g. wet weight) was disrupted in a Pascall Triple Roll Mill No. 1 and suspended in 100 ml. of 0.03 M — phosphate buffer, pH 7.0. After centrifugation at 15000 g for 30 minutes to remove cell debris, the supernatant was centrifuged 78,480 g for 90 minutes. The pellets were taken up in 0.03 M — phosphate buffer, pH 7.0 (1.0 ml. total) and debris was removed by centrifugation at 7000 g for 20 minutes. The resultant crude virus preparation was further purified by rate zonal centrifugation on linear gradients of sucrose (10 – 50%) at 69,000 g for 2 hours. A well-defined blue grey, light scattering band, was collected and dialysed exhaustively against 0.03 M phosphate buffer, pH 7.4. Examination by electron microscopy (J.E.M. Model 7) showed this preparation to contain polyhedral particles approximately 40–42 nm. in diameter, having an appearance compatible with icosahedral symmetry.

Particles obtained from *Aspergillus niger* strain IMI 146891, by essentially the same procedure, were morphologically similar to the particles obtained from *Aspergillus foetidus*.

The crude virus preparations were purified by isopycnic centrifugation on preformed gradients of caesium chloride using the Beckman SW 27 rotor at 25,000 r.p.m. for 18 hours. Four bands all of which contained intact virus particles when examined electron microscopically, were obtained in the density range 1.34 – 1.40. The four bands were collected and pooled, and dialysed exhaustively against 0.03 M sodium phosphate buffer, pH 7.4, containing 0.1 M — sodium chloride. Such preparations showed single boundary (S≈156s)

when centrifuged at 40,000 g in a Beckman Model E Analytical Ultracentrifuge and examined with the ultra violet scanner or with schlieren optics, and had an ultra violet spectrum characteristic of nucleoprotein ($\lambda_{max}$260 nm., $\lambda_{min}$245 nm, 260:280 ratio 1.50).

Nucleic acid was extracted from purified virus preparations from both strains of mould using the phenol-sodium dodecyl sulphate method essentially as described by Franklin (Proc. U.S. Nat. Acad. Sci., 55,1504 (1966). The ultraviolet spectrum of the product was characteristic of nucleic acid with $\lambda_{max}$258 nm. $\lambda_{min}$235 nm., 260:280 ratio 2.26. The nucleic acid was characterised as RNA by hydrolysis with 0.3 N — sodium hydroxide at 37° for 18 hours; the nucleotides formed in high yield were identified by their electrophoretic mobilities in 0.05 M — ammonium formate buffer, pH 3.5, and their ultraviolet spectra, as uridylic acid, guanylic acid, cytidylic acid and adenylic acid.

The viral RNA from the virus preparations from both strains of mould was shown to be double-stranded by its characteristic melting curves and by the treatment with ribonuclease.

Both the virus particles and viral double-stranded RNA were potent inducers of interferon in mice.

An intraperitoneal injection of 10γRNA from *Aspergillus foetidus* IMI 41871 in its free state or as virus-like particles in physiological saline (0.1 ml) was administered to 18–22g mice (Strain CD1). Twenty four hours later these mice were challenged with varying dilutions of encephalomyocarditis, Coxsackie B1 or Semliki Forest, viruses administered by the intraperitoneal route. The mortality ratio and mean survival times of treated mice were compared with those of untreated control mice. The mean survival time was calculated as follows:

$$\frac{N}{\epsilon \frac{n}{x}} = S.T.$$

where
N = Number of animals in group
n = number of animals dying on day x.

Summary of results

TABLE 1

| Encephalomyocarditis virus | | | | | | |
|---|---|---|---|---|---|---|
| Dilution of challenge virus | Double-stranded RNA | | Double-stranded RNA as virus-like particles | | Controls | |
| | Mortality | Survival time | Mortality | Survival time | Mortality | Survival time |
| $10^2$ | 9/10 | 7.1 | 9/10 | 6.8 | — | — |
| $10^3$ | 5/10 | 12.0 | 5/10 | 10.7 | 10/10 | 3.9 |
| $10^4$ | 3/10 | 17.8 | 0/10 | ∞ | 10/10 | 4.3 |
| $10^5$ | 0/10 | ∞ | 0/10 | ∞ | 6/10 | 7.1 |
| $LD_{50}$ (Reed & Muench) | $10^{-3.20}$ | | $10^{-2.9}$ | | $10^{-5.4}$ | |

TABLE 1-continued

| Encephalomyocarditis virus | | | | | | |
|---|---|---|---|---|---|---|
| Dilution of challenge virus | Double-stranded RNA | | Double-stranded RNA as virus-like particles | | Controls | |
| | Mortality | Survival time | Mortality | Survival time | Mortality | Survival time |

| Semliki Forest Virus | | | | | | |
|---|---|---|---|---|---|---|
| Dilution of challenge virus | Double-stranded RNA | | Double-stranded RNA as virus like particles | | Controls | |
| | Mortality | Survival time | Mortality | Survival time | Mortality | Survival time |
| $10^2$ | 7/10 | 9.4 | 7/10 | 7.9 | 10/10 | 4.6 |
| $10^3$ | 10/10 | 6.6 | 9/10 | 8.4 | 10/10 | 4.7 |
| $10^4$ | 4/10 | 22.5 | 7/10 | 12.5 | 10/10 | 6.1 |
| $10^5$ | 1/10 | 80.0 | 3/10 | 22.9 | 9/10 | 6.0 |
| $LD_{50}$ (Reed & Muench) | $10^{-3.7}$ | | $10^{-4.2}$ | | $10^{-6.7}$ | |

| Coxsackie B1 Virus | | | | | | |
|---|---|---|---|---|---|---|
| Dilution of challenge virus | Double-stranded RNA | | Double-stranded RNA as virus like particles | | Controls | |
| | Mortality | Survival time | Mortality | Survival time | Mortality | Survival time |
| $10^1$ | 4/10 | 12.2 | 6/10 | 9.0 | 9/10 | 4.2 |
| $10^2$ | 4/10 | 13.6 | 3/10 | 16.2 | 4/10 | 10.0 |
| $10^3$ | 0/10 | ∞ | 0/10 | ∞ | 2/10 | 34.0 |
| $LD_{50}$ (Reed & Muench) | $10^{-1.2}$ | | $10^{-1.4}$ | | $10^{-1.9}$ | |

EXAMPLE 2

We have also noted the presence of virus particles in *Aspergillus foetidus* IMI 130408 and IMI 50566 and in *Aspergillus niger*.

What is claimed is:

1. A process for the production of double-stranded ribonucleic acid or the sodium salt thereof which comprises deproteinizing virus particles extracted from *Aspergillus foetidus* or *Aspergillus niger* and recovering the double-stranded ribonucleic acid or sodium salt thereof obtained.

2. A process according to claim 1 wherein the deproteinization comprises treating the virus particles with a detergent and phenol.

3. A process according to claim 2 wherein the deproteinization comprises adding sodium dodecyl sulphate to an aqueous suspension of virus particles, extracting the resulting suspension with phenol, separating the resulting aqueous phase by centrifugation, extracting the phenol and precipitating the double-stranded ribonucleic acid or sodium salt thereof of.

4. A process according to claim 3 wherein the double-stranded ribonucleic acid or sodium salt thereof is precipitated by adding an alcohol.

5. A process according to claim 3 for the production of double-stranded ribonucleic acid wherein the precipitation step comprises precipitating the double-stranded ribonucleic acid in the form of the acid.

6. A process according to claim 3 for the production of the sodium salt of double-stranded ribonucleic acid which comprises treating the culture medium with the sodium salt of ribonucleic acid obtained from yeast.

* * * * *